United States Patent [19]

Ogata et al.

[11] Patent Number: 5,098,898
[45] Date of Patent: Mar. 24, 1992

[54] PHOSPHOLIPID DERIVATIVES

[75] Inventors: Kazumi Ogata, Toyonaka; Kyozo Yamamoto, Higashiosaka; Takahiro Matsumoto, Akashi, all of Japan

[73] Assignee: Senju Pharmaceutical Co., Ltd., Osaka, Japan

[21] Appl. No.: 635,620

[22] PCT Filed: Apr. 24, 1990

[86] PCT No.: PCT/JP90/00534

§ 371 Date: Dec. 27, 1990

§ 102(e) Date: Dec. 27, 1990

[87] PCT Pub. No.: WO90/12800

PCT Pub. Date: Jan. 11, 1990

[30] Foreign Application Priority Data

Apr. 27, 1989 [JP] Japan ................... 1-109992

[51] Int. Cl.$^5$ ...................... A61K 31/665; C07F 9/06
[52] U.S. Cl. ...................... 514/99; 549/222
[58] Field of Search .................. 549/222; 514/99

[56] References Cited

U.S. PATENT DOCUMENTS 4,647,672 3/1987 Seib et al. ................. 549/222
5,013,850 5/1991 Lee ......................... 549/222

FOREIGN PATENT DOCUMENTS 339486 11/1989 European Pat. Off. ............ 549/222
12800 11/1990 World Int. Prop. O. .......... 549/222

Primary Examiner—Cecilia Shen
Attorney, Agent, or Firm—Wenderoth, Lind & Ponack

[57] ABSTRACT

Phospholipid derivatives resulting from coupling of ascorbic acid to a glycerol ester or ether via a phosphoric acid residue and having antioxidant activity and lipid peroxide inhibiting activity, which have the formula

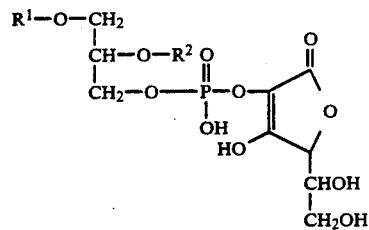

or

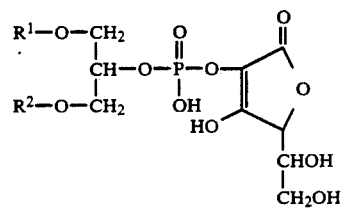

wherein $R^1$ and $R^2$ represent the same or different and each represents an alkyl or acyl group and neither formula represents any particular configuration nor conformation.

4 Claims, No Drawings

PHOSPHOLIPID DERIVATIVES

TECHNICAL FIELD

This invention relates to a novel phospholipid derivative, a method of producing the same and uses therefor, including pharmaceutical application thereof.

BACKGROUND ART

While a compound composed of ascorbic acid and alpha-tocopherol coupled together via a phosphoric acid residue is disclosed in Japanese Kokai Tokkyo Koho (published unexamined patent application) No. 59-219295, no compound comprising a phospholipid and ascorbic acid is known as yet.

It is believed that active oxygen and lipid peroxides are factors causative of aging, adult diseases and other diseases, hence are harmful to living bodies, and should be eliminated from living bodies. For inhibiting the formation or decomposing these hazardous substances, the use of antioxidants originally occurring in living organisms, for example vitamin E, ascorbic acid, ubiquinone and uric acid, has been proposed. However, none of them is fully satisfactory.

DISCLOSURE OF THE INVENTION

The present inventors made investigations concerning ascorbic acid derivatives. As a result, they succeeded in synthesizing certain phospholipid-type ascorbic acid derivatives resulting from binding a glycerol ester or ether to ascorbic acid via a phosphoric acid residue and found that said derivatives have antioxidant activity and lipid peroxide inhibiting activity, among others. The present invention has been completed based on such and other findings.

In one aspect thereof, the present invention provides phospholipid derivatives of the formula

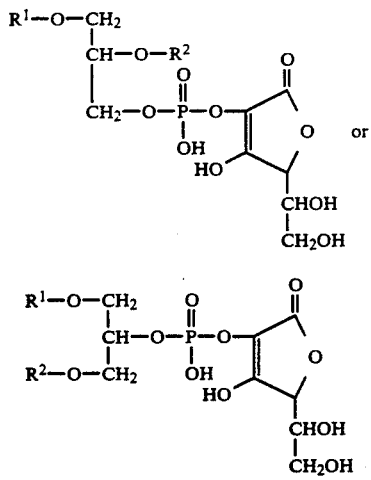

wherein $R^1$ and $R^2$ represent the same or different and each represents an alkyl or acyl group. It is to be noted that neither formula represent any specific configuration nor conformation.

In formulas [I] and [II], the alkyl or acyl group represented by $R^1$ and/or $R^2$ preferably contains 1 to 18 carbon atoms. The carbon chain in the alkyl group or the acyl group when it is an aliphatic acyl may be straight or branched or cyclic and may contain a cyclic portion. As examples of the alkyl group, there may be mentioned lower alkyl groups, such as methyl, ethyl, n-propyl, i-propyl, n-butyl, t-butyl, sec-butyl, n-pentyl, 1-ethylpropyl and i-pentyl, as well as higher alkyl groups, such as n-decyl, n-undecyl, n-pentadecyl, n-hexadecyl, n-heptadecyl, n-octadecyl, and isomeric forms of these. As the acyl group, there may be mentioned, for instance, acyclic acyl groups, such as acetyl and propionyl, and cyclic acyl groups, such as cyclopentylcarbonyl and cyclohexylcarbonyl. The acyl group may be also be an aromatic or araliphatic acyl group, such as benzoyl or phenylacetyl.

In another aspect, the invention provides a method of producing phospholipid derivatives of the formula [I] or [II] given above which comprises reacting a glycerol halophosphate derivative of the formula

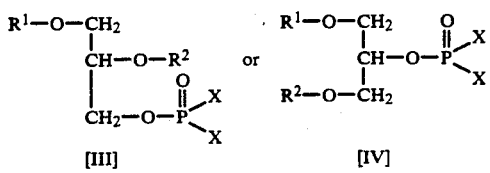

wherein $R^1$ and $R^2$ represent as defined above, X represents a halogen atom and neither formula represent any particular configuration nor conformation, with ascorbic acid protected at positions 5 and 6 and then deprotecting said positions 5 and 6.

The glycerol halophosphate derivatives mentioned above can be prepared by reacting a glycerol diester, diether or monoester monoether compound of the formula

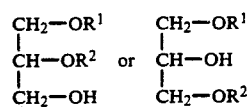

wherein $R^1$ and $R^2$ represent defined above and neither formula indicates any specific steric configuration, namely a compound derived from glycerol by substitution of $R^1$ and $R^2$ for two of the three hydroxyl groups of glycerol, with a halophosphorylating agent, for example a phosphorous oxyhalide, such as phosphorous oxychloride or phosphorus oxybromide, in the presence of a deacidifying agent. An organic amine, such as triethylamine or pyridine, is preferred as the deacidifying agent.

The protective group for protecting the 5- and 6-position of ascorbic acid should desirably be eliminable readily after the reaction and an isopropylidene group or the like is a preferred example although an acyl group such as acetyl may also be used.

The reaction of the protected ascorbic acid and the glycerol halophosphate ester can proceed under mild conditions, for example at 0° C. to room temperature, in a nonpolar solvent, such as tetrahydrofuran (THF), in the presence of a deacidifying agent, such as pyridine or triethylamine.

The deprotection reaction can be carried out under mild conditions. Thus, for example, the protective group can be readily eliminated by acidifying the reaction mixture with an inorganic acid, such as hydrochloric acid, phosphoric acid or sulfuric acid, or an organic acid, such as acetic acid or citric acid.

In a further aspect thereof, the invention provides an antioxidant composition comprising a phospholipid derivative of the above formula [I] or [II].

The research done by the inventors of the present invention revealed that both compounds [I] and [II] have antioxidant activity (cf. Test Example).

Studies made by the present inventors have revealed that the compound [I] or [II] can be used for various purposes in the form of a free acid or a nontoxic salt, for example an alkali metal salt (e.g. sodium salt, potassium salt) or an alkaline earth metal salt (e.g. calcium salt, magnesium salt).

The compounds according to the invention are used as biologically active antioxidants for the prevention or treatment of ischemic organ disorders. They are administered in dosage forms suited for oral or nonoral application. They are also expected to be effective against cataract, skin disease (e.g. atopic dermatitis, urticaria, ultraviolet-induced inflammation) and so on.

The dosage forms include external preparations (e.g. ointments, ophthalmic solutions, nasal preparations, creams), injectable solutions, preparations for internal use, and so forth. These preparations may contain ingredients in ordinary use, for example fillers or excipients, binders, wetting agents, disintegrants, lubricants, dispersants, buffers, surfactants, isotonizing agents, stabilizers and pH adjusting agents. Furthermore, the compounds can be incorporated into cosmetics.

The dose may be vary depending on the compound, dosage form, symptom to be treated or prevented and other factors. Generally, however, the preparations mentioned above should preferably contain about 0.01 to 5%, more preferably about 0.1 to 3%, of the compound [I] or [II]. In the case of injectable solutions, for instance, the daily dose may amount to 0.1 to 20 mg, which is to be administered as a single dose; in the case of preparations for internal use, a dose of 1 to 100 mg may be administered several times a day; the external preparations may take the form of 0.1 to 3% ointments, for instance.

The compounds according to the invention may also be added as antioxidants to foodstuffs, such as butter, margarine, soybean oil and other oils, and processed fish or flesh products, for the prevention of degradation thereof. The level of addition may vary depending on the foodstuff and/or the specific compound. Generally, however, said level is recommendably in the range of 0.01 to 5%, preferably about 0.02 to 3%.

The antioxidant composition according to the invention may further contain another or other antioxidant ingredients and/or one or more pharmacologically active ingredients.

TEST EXAMPLE

Antioxidant Activity

Several typical examples of the compound according to the invention were tested for antioxidant activity according essentially to the Stocks' method.

Male Wistar rats (about 10 weeks old) were used. After perfusion for removing the blood from the brain, brain tissues were excised and homogenized in 4 weights of 0.1M phosphate-buffered saline (pH 7.4) with water cooling. The homogenate was centrifuged at 1,000×g for 10 minutes and the supernatant was used. The brain homogenate supernatant was diluted with 10 volumes of phosphate-buffered saline and 500 μl of the dilution was incubated at 37° C. for 60 minutes. The reaction was terminated by dipping the test tube into ice. After further addition 490 μl of 0.1M phosphate-buffered saline, assay was performed by the TBA method. The quantity of lipid peroxides (LPO) was expressed in terms of amount of malonedialdehyde (MDA) per milligram of protein. For protein assay, the Lowry method was used.

Test compounds (1) 1,2-O-Distearoyl-3-glycerophosphoryl-ascorbic acid (2) 1,2-O-Dipalmitoyl-3-glycerophosphoryl-ascorbic acid (3) 1,2-O-Dihexadecyl-3-glycerophosphoryl-ascorbic acid (4) 1,2-O-Dilauroyl-3-glycerophosphoryl-ascorbic acid potassium salt (5) 1,3-O-Dilauroyl-2-glycerophosphoryl-ascorbic acid potassium salt

Test results

|     | Dose (M) | Inhibition (%) |
| --- | --- | --- |
| (1) | $1 \times 10^{-3}$ | 100 |
|     | $1 \times 10^{-4}$ | 100 |
|     | $1 \times 10^{-5}$ | 25.7 |
| (2) | $1 \times 10^{-3}$ | 100 |
|     | $1 \times 10^{-4}$ | 100 |
|     | $1 \times 10^{-5}$ | 55.9 |
| (3) | $1 \times 10^{-3}$ | 100 |
|     | $1 \times 10^{-4}$ | 100 |
|     | $1 \times 10^{-5}$ | 70.4 |
| (4) | $1 \times 10^{-3}$ | 97.8 |
|     | $1 \times 10^{-4}$ | 100 |
|     | $1 \times 10^{-5}$ | 8.6 |
| (5) | $1 \times 10^{-3}$ | 100 |
|     | $1 \times 10^{-4}$ | 82.2 |
|     | $1 \times 10^{-5}$ | 20.1 |
|     | Ascorbic acid | |
|     | $1 \times 10^{-3}$ | −22.9 |
|     | $1 \times 10^{-4}$ | −28.6 |
|     | Vitamin E | |
|     | $1 \times 10^{-3}$ | 94.3 |
|     | $1 \times 10^{-4}$ | 62.9 |
|     | $1 \times 10^{-5}$ | 28.6 |

As is evident from the above test results, the compounds according to the invention are comparable or superior in antioxidant activity to vitamin E, while ascorbic acid rather promoted oxidation.

BEST MODES FOR CARRYING OUT THE INVENTION

The following examples further illustrate the invention.

Starting Material Synthesis 1

3-O-Benzylglycerol

The 50 ml of a 50% (w/v) sodium hydroxide solution are added 33 g (0.25 mole) of isopropylideneglycerol, 30.25 ml (0.25 mole) of benzyl chloride and 1.38 g (4 millimoles) of benzoyl chloride and 1.38 g (4 millimoles) of benzyltri-n-butylammonium. The mixture is stirred at 100° C. for 5 hours, then cooled to room temperature, diluted with 50 ml of water and extracted with ether. The extract is washed with water and then the solvent is distilled off under reduced pressure. To the residue is added 70 ml of 15% (w/v) sulfuric acid, and the mixture is stirred at 100° C. for 2.5 hours. After cooling, the unreacted material is removed by extraction with petroleum ether, the aqueous layer is neutralized and then extracted with ethyl acetate, and the extract is washed with a saturated sodium chloride solution and dried over anhydrous sodium sulfate. The solvent is then distilled off under reduced pressure to give about 21 g of a yellow oil.

Starting Material Synthesis 2

1,2-O-Distearoyl-3-O-benzylglycerol

3-O-Benzylglycerol (18.2 g, 0.1 mole) and 17 ml of dry pyridine are dissolved in 50 ml of dry benzene. To the solution is added dropwise a solution of 60 g (0.2 mole) of stearoyl chloride in 100 ml of dry benzene with cooling and stirring. After completion of the dropping, the mixture is stirred at 60°–70° C. for 24 hours. The reaction mixture is then extracted with ether, the extract is washed in sequence with water, 0.2N sulfuric acid, saturated sodium hydrogen carbonate and water and dried over anhydrous sodium sulfate. The solvent is distilled off under reduced pressure, ethanol is added to the residue and the mixture was allowed to cool. The resulting crystalline precipitate is collected by filtration and recrystallized from ethanol to give 32 g of white crystals. Melting point: 52°–54° C.; IR spectrum (KBr): 2900, 2840, 1720, 1180, 720 cm$^{-1}$.

Starting Material Synthesis 3

1,2-O-Dipalmitoyl-3-O-benzylglycerol

3-O-Benzylgylcerol (18.2 g) is reacted with 55 g of palmitoyl chloride in the same manner as in Starting Material Synthesis 2. Recrystallization of the crude crystals from ethanol gives 52 g of white crystals. Melting point: 40°–42° C.

Starting Material Synthesis 4

1,2-O-Dilauroyl-3-benzylglycerol

3-O-Benzylglycerol (7 g) is reacted with 18.5 g of lauroyl chloride in the same manner as in Starting Material Synthesis 2. Recrystallization of the crude crystals from ethanol gives 16 g of white crystals. Melting point: 30°–31° C.

Starting Material Synthesis 5

1,2-O-distearoylglycerol 1,2-O-distearoyl-3-O-benzylglycerol (22 g, 0.03 mole) is dissolved in 300 ml of n-hexane, 3 g of 10% palladium-on-carbon is added, and catalytic reduction is conducted at room temperature. When hydrogen absorption has ceased, the catalyst is filtered off and the solvent is distilled off under reduced pressure. The resulting crystalline precipitate is collected by filtration and recrystallized from white acetate to give 13 g of white crystals. Melting point: 66°–67° C.; IR spectrum (KBr): 3500, 2900, 2850, 1730, 1460, 1180, 720 cm$^{-1}$.

Starting Material Synthesis 6

1,2-O-Dipalmitoyl-3-benzylglycerol 1,2-O-Dipalmitoyl-3-O-benzylglycerol (20 g) is treated in the same manner as in Starting Material Synthesis 5. Recrystallization of the crude crystals from n-hexane-ethanol gives 16 g of white crystals. Melting point: 62°–63° C.; IR spectrum (KBr): 3500, 2900, 2840, 1740, 1465, 1180, 720 cm$^{-1}$.

Starting Material Synthesis 7

1,2-O-Dilauroylglycerol 1,2-O-Dilauroyl-3-O-benzylglycerol (16 g) is treated in the same manner as in Starting Material Synthesis 5 and the crude crystals are recrystallized form ethanol to give 12 g of white crystals. Melting point: 64°–66° C.; IR spectrum (KBr): 3500, 2920, 2850, 1725, 1710, 1215, 1195, 720 cm$^{-1}$.

Starting Material Synthesis 8

1,2-O-Dihexadecyl-3-O-benzylglycerol

3-O-Benzylglycerol (9.0 g, 0.05 mole) and 25 g (0.08 mole) of 1-bromohexadecane are dissolved in 50 ml of dry benzene, 8.8 g (0.16 mole) of potassium hydroxide is added to the solution, and the mixture is heated under reflux with stirring for 16 hours. The reaction mixture is neutralized by adding hydrochloric acid then extracted with 50 ml of ethyl acetate. The extract is washed in sequence with 2.5% potassium hydrogen carbonate and water and dried over anhydrous sodium sulfate. The solvent is then distilled off under reduced pressure to give 35 g of an oily residue.

Starting Material Synthesis 9

1,2-O-Dihexadecylglycerol 1,2-Dihexadecyl-3-O-benzylglycerol (35 g) is treated in the same manner as in Starting Material Synthesis 5 and the crude crystals are recrystallized from ethanol to give 7.2 g of white crystals. Melting point: 49°–50° C.; IR spectrum (KBr): 3480, 2920, 2850, 1470, 1120, 1080 cm$^{-1}$.

EXAMPLE 1

1,2-O-Distearoyl-3-glycerophosphoryl-ascorbic acid

Dry benzene (40 ml) is added to 3.15 g (5 millimoles) of 1,2-O-distearoylglycerol and 2 ml of dry pyridine. To the resulting solution is added dropwise a solution of 1.6 g of phosphorus oxychloride in 20 ml of dry benzene with ice cooling for 30 minutes and then at room temperature for 6 hours. The reaction mixture is concentrated under reduced pressure. Benzene (20 ml) is added to the residue for dissolution thereof. Separately, 3.3 g (15 millimoles) of isopropylidene-ascorbic acid and 3 ml of dry pyridine are dissolved in 50 ml of dry tetrahydrofuran. To this mixed solution is added dropwise the above benzene solution. The resulting mixture is stirred with ice cooling for 30 minutes and then at room temperature for 16 hours. The reaction mixture is concentrated under reduced pressure. To the thus-obtained oily residue (about 10 g) are added 100 ml of ethanol and 60 ml of 1N hydrochloric acid. The mixture is stirred at 60° C. for 30 minutes for deacetonation, then cooled and extracted with ethyl acetate. The extract is washed with a saturated aqueous sodium chloride solution and dried over anhydrous sodium sulfate, and the solvent is distilled off under reduced pressure. Acetone is added to the residue, the mixture is allowed to cool, and the resulting crystalline precipitate is collected by filtration and recrystallization from ethanol-acetone to give 1.5 g of white crystals.

Melting point: 98°–100° C.

Elemental analysis: Calculated for $C_{45}H_{83}O_{13}P$: C, 62.62%; H, 9.69%; Found: C, 62.53%; H, 9.61%

Silica gel thin layer chromatography (developing solvent: chloroform-methanol-acetic acid-water=30:10:2:1): R$_f$=0.58.

IR spectrum (KBr): 3900 (broad), 2910, 2840, 1740, 1470, 1105 cm$^{-1}$

EXAMPLE 2

1,2-O-Dipalmitoyl-3-glycerophosphorylascorbic acid 1,2-O-Dipalmitoylglycerol (2.9 g) is treated in the same manner as in Example 1. Recrystallization from ethanol-acetone gives 1.8 g of white crystals. Melting point: 95°–97° C.; silica gel thin layer chromatography (developing solvent: chloroform-methanol-acetic acid-water=30:20:2:1): R$_f$=0.55; IR spectrum (kBr): 3400 (broad), 2920, 2850, 1740, 1470, 1060 cm$^{-1}$.

EXAMPLE 3

1,2-O-Dihexadecyl-3-glycerophosphorylascorbic acid 1,2-O-Dihexadecylglycerol (2.7 g) is treated in the same manner as in Example 1. Recrystallization from ethanol-acetone gives 1.7 g of white crystals. Melting point: 61°–63° C.; silica gel thin layer chromatography (developing solvent: chloroform-ethanol-acetic acid-water=30:20:2:1): Rf=0.53; IR spectrum (KBr): 3400 (broad), 2925, 2850, 1470, 1130 cm$^{-1}$.

EXAMPLE 4

1,2-O-Dilauroyl-3-glycerophosphorylascorbic acid potassium salt 1,2-O-Dilauroylglycerol (4.6 g) is treated in the same manner as in Example 1. The desired product obtained as an oil dissolved in 100 ml of ethanol. To the solution is added dropwise gradually an ethanolic solution of potassium hydroxide until the solution of potassium hydroxide until the solution assumes a neutral pH, whereupon white crystals precipitate out. The crystals are collected by filtration and recrystallized from cyclohexane-acetone to give 3.5 g of white crystals. Melting point: 100°–102° C.; silica gel thin layer chromatography (developing solvent: chloroform-methanol-acetic acid-water=30:10:2:1): R$_f$=0.71; IR spectrum (KBr): 3400 (broad), 2920, 1850, 1730, 1600, 1240, 1095 cm$^{-1}$.

EXAMPLE 5

1,3-O-Dilauroyl-2-glycerolphosphorylascorbic acid potassium salt 1,3-O-Dilauroylglycerol (4.5 g) is treated in the same manner as in Example 4. Recrystallization from cyclohexane-acetone gives 3.5 g of white crystals. Melting point: 102°–104° C.; thin layer chromatography (developing solvent: chloroform-methanol-acetic acid-water=30:10:2:1): R=0.73; IR spectrum (KBr): 3400 (broad), 2930, 1850, 1730, 1600, 1240, 1095 cm$^{-1}$.

EXAMPLE 6

1,3-O-Diethyl-2-glycerophosphorylascorbic acid 1,3-O-Diethylglycerol (4.4 g) is treated in the same manner as in Example 1 to give an oil. This oil is purified by silica gel column chromatography (Merck, Art 9385, 200 g; developing solvent: chloroform-methanol-acetic acid-water=30:10:2:1) to give about 3 g of the desired compound as an oil. Silica gel thin layer chromatography (developing solvent: chloroform-methanol-acetic acid-water=30:10:2:1) R$_f$=0.59; IR spectrum (neat): 3450 (broad), 2960, 1765, 1690, 1390, 1220, 1070 cm$^{-1}$.

The following dosage form examples are further illustrative of the present invention.

DOSAGE FORM EXAMPLE 1

Tablets for Internal Use

| | |
|---|---|
| 1,2-O-Diestearoyl-3-glycerophosphorylascorbic acid | 30 g |
| Lactose | 40 g |
| Corn starch | 50 g |
| Potato starch | 20 g |
| Talc | 12 g |
| Magnesium stearate | 8 g |
| Total | 160 g |

Tablets each weighing 160 mg are produced in the conventional manner using the above ingredients. They may be sugar-coated as necessary.

DOSAGE FORM EXAMPLE 2

Injection

| | |
|---|---|
| 1,2-O-Dipalmitoyl-3-glycerolphosphoryl-ascorbic acid potassium salt | 200 mg |
| Disodium hydrogen phosphate | 120 mg |
| Monosodium dihydrogen phosphate | 80 mg |
| Glucose | 5 g |
| Distilled water for injection | To make 100 ml |

An injectable solution is prepared in the conventional manner using the above ingredients. The solution is sterilized by bacterial filtration and distributed in 2-ml portions into glass ampoules, which are then sealed.

DOSAGE FORM EXAMPLE 3

Ophthalmic solution

| | |
|---|---|
| 1,2-O-Dihexadecyl-3-glycerophosphoryl-ascorbic acid potassium salt | 100 mg |
| Boric acid | 1.8 g |
| methyl p-hydroxybenzoate | 160 mg |
| Propyl p-hydroxybenzoate | 140 mg |
| 1 N sodium hydroxide | q.s. |
| Sterilized pure water | To make 100 ml |

An ophthalmic solution is prepared in the conventional manner using the above ingredients.

DOSAGE FORM EXAMPLE 4

| | |
|---|---|
| 1,3-O-Dilauroyl-3-glycerophosphorylascorbic acid potassium salt | 1 g |
| Hydropholic ointment base | To make 100 g |

An ointment is produced in the conventional manner using the above ingredients.

DOSAGE FORM EXAMPLE 5

| | |
|---|---|
| 1,2-O-Distearoyl-2-glycerophosphoryl ascorbic acid potassium salt | 0.5 g |
| Stearic acid | 2.0 g |
| Stearyl alcohol | 7.0 g |
| Squalane | 5.0 g |
| Octyldecanol | 6.0 g |
| Polyoxyethylene (15) cetyl ether | 3.0 g |
| Glycerol monostearate | 2.0 g |
| Propylene glycol | 5.0 g |
| Methyl p-hydroxybenzoate | 0.2 g |
| Propyl p-hydroxybenzoate | 0.1 g |

| | |
|---|---|
| -continued | |
| Sterilized pure water | To make 100 g |

A cream is produced in the conventional manner using the above ingredients.

INDUSTRIAL APPLICABILITY

The phospholipid derivatives according to the invention have antioxidant activity and therefore are useful as biological active antioxidants in the prevention or treatment of ischemic organ diseases. They can also be used effectively in the treatment of cataract, skin diseases (e.g. atopic dermatitis, urticaria, ultraviolet-induced inflammation) and so forth.

Furthermore, they can be used advantageously as antioxidants for preventing foodstuffs from degrading.

We claim:

1. A phospholipid compound of the formula

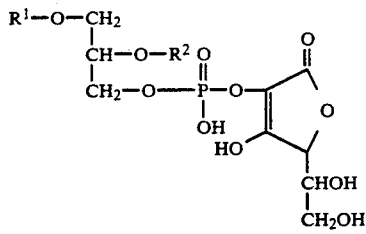

or

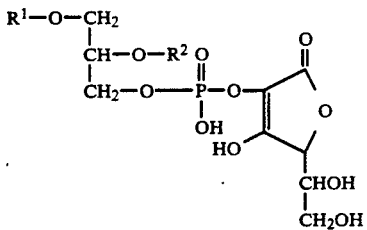

wherein $R^1$ and $R^2$ represent the same or different and each represents an alkyl or acyl group, said acyl group selected from the group consisting of acyclic, cyclic, aromatic and araliphatic acyl groups derived from carboxylic acids, and neither formula representing any particular configuration or conformation.

2. A compound as claimed in claim 1, wherein $R^1$ and/or $R^2$ is a $C_{1-18}$ alkyl or acyl group.

3. An antioxidant composition which comprises a phospholipid compound of the formula $R^1$—O—CH$_2$
|
CH—O—R$^2$   O
|              ||
CH$_2$—O——P—O
              |
              OH    HO
                         CHOH
                         |
                         CH$_2$OH or $R^1$—O—CH$_2$    O
|                 ||
CH—O—P—O
|         |
$R^2$—O—CH$_2$  OH
                HO
                         CHOH
                         |
                         CH$_2$OH wherein $R^1$ and $R^2$ represent the same or different and each represents an alkyl or acyl group, said acyl group selected from the group consisting of acyclic, cyclic, aromatic and araliphatic acyl groups derived from carboxylic acids, and neither formula represents any particular configuration or conformation.

4. The composition according to claim 3, wherein $R^1$ and/or $R^2$ is a $C_{1-18}$ alkyl or acyl group.

* * * * *